United States Patent [19]

Kamada et al.

[11] Patent Number: 5,469,255
[45] Date of Patent: Nov. 21, 1995

[54] METHOD AND APPARATUS FOR SPECTROMETRIC MEASUREMENT OF PARTICULATE SURFACES

[76] Inventors: Kenji Kamada, Seciel-Uzumasa 206, 16-3, Uzumasa Miyamae-cho, Ukyo-ku, Kyoto-shi, Kyoto; Keiji Sasaki, 14-12, Koaza Toriimae, Aza Enmyoji, Oyamazaki-cho, Otokuni-gun Kyoto; Noboru Kitamura, Mezon-Takano 502, 34-35, Tanaka Kamifurukawa-cho, Sakyo-ku, Kyoto-shi, Kyoto; Hiroshi Masuhara, 2-4-16, Minamikonoeke-cho, Higashi-Osaka-shi, Osaka, all of Japan

[21] Appl. No.: 186,991

[22] Filed: Jan. 27, 1994

[30] Foreign Application Priority Data

Jan. 28, 1993 [JP] Japan ..................... 5-012957
Jan. 28, 1993 [JP] Japan ..................... 5-012958

[51] Int. Cl.[6] .......................... G01J 3/42; G01J 3/443
[52] U.S. Cl. .................... 356/300; 356/318; 250/458.1
[58] Field of Search ....................... 356/300, 317, 356/318, 417; 250/458.1, 459.1, 461.1, 461.2

[56] References Cited

U.S. PATENT DOCUMENTS 5,212,382  5/1993  Sasaki et al. .................... 250/251
5,283,417  2/1994  Misawa et al. .................... 219/121.85

OTHER PUBLICATIONS

Kamada et al., "Microparticle Laser: Temporal characteristics and Intractivity Absorption Effects", in *Abstracts of 6th Symposium on Unconventional Photoactive Solids*, Aug. 1993.

Kamada et al., "Picosecond Lasing Dynamics of an Optically Trapped Microparticle", in *Abstracts of KUL–JRDC Joint Symposium on Spectroscopy and Chemistry in Small Domains*, Aug. 1994.

Kamada et al., "Trapping Single–Particulate by Laser Beam, and Laser Emission Applications for Transient Absorption Measurment in Particulates", in *Abstracts of 65th Spring conference of the Chemical Society of Japan*, Apr. 1993.

Kamada et al., "Measurement of Transient Absorption Micro–Area of Single Particulates by Laser Emission", in *Abstracts of Conference on Molecular Structure*, Oct. 1993.

Misawa et al., "Chemistry Letters", Chemical Society of Japan, pp. 1479–1482, 1990.

*Primary Examiner*—F. L. Evans
*Attorney, Agent, or Firm*—Wenderoth, Lind & Ponack

[57] ABSTRACT

A method of spectrometry is disclosed for measuring transient absorbance and transient absorption spectrum of a substance to be measured at interfaces in liquid phase of particulates containing a fluorescent pigment and the substance to be measured by the utilization of optical resonance phenomenon. An apparatus for carrying out the method is also disclosed and comprises: (a) a pulse laser oscillator for exciting the fluorescent pigment and the substance to be measured, respectively; (b) an optical delay device for causing delay of any one of pulse laser beams of two kinds of wavelengths generated by the pulse laser oscillator; (c) a microscope system for condensing laser beams generated by the pulse laser oscillator and irradiating the condensed beams to the sample; and (d) a detector for detecting light emission of the sample. According to the method of the present invention, it is possible to measure transient absorbance and transient absorption spectrum at a high sensitivity even when particulates containing the substance to be measured in liquid phase are present.

5 Claims, 3 Drawing Sheets

METHOD AND APPARATUS FOR SPECTROMETRIC MEASUREMENT OF PARTICULATE SURFACES

FIELD OF THE INVENTION

The present invention relates to a method of spectrometry and an apparatus therefor. More particularly, the present invention relates to a method of spectrometry and an apparatus therefor, which are useful for spectrometric measurement of the surfaces of particulates in such areas as chemicals, foods, pharmaceuticals, materials and electronics.

DESCRIPTION OF PRIOR ART

Analyzing physical properties and reaction mechanisms at interfaces between particulates and the surrounding medium thereof has now become a very important problem for the development of new technologies and new products in such various areas as chemicals, foods, pharmaceuticals, materials and electronics. For the purpose of analyzing the status of such surfaces, spectrometry is usually applied, and for this spectrometry, fluorescent spectrometry and transient absorbance spectrometry are known.

However, the fluorescent spectrometry, being a measuring method permitting high-sensitivity measurement, requires the substance to be measured to be fluorescent. The scope of application of the fluorescent spectrometry is therefore limited.

For the transient absorbance spectrometry, on the other hand, while it is applicable for analysis of intermediate products of photochemical reactions, the detection sensitivity is so low that, in measurement of absorbance of a substance contained in particulates having a particle size of the micrometer order, for example, it is impossible to achieve a sufficient absorbance because of the short length of optical path.

It has therefore been impossible to conduct spectrometry permitting a high accuracy analysis of particulate properties by the conventional fluorescent spectrometry or transient absorbance methods.

The present invention was developed to solve these problems in the conventional methods as described above, and has an object to provide a novel method of spectrometry and an apparatus therefor, which permits spectrometric measurement of the condition of interfaces of particulates at a high accuracy even when particulates containing a substance to be measured is present in liquid phase.

SUMMARY OF THE INVENTION

To solve the above-mentioned problems, the present invention provides a method of spectrometry for measuring transient absorbance and transient absorption spectrum of a substance to be measured at interfaces of particulates containing a fluorescent pigment and the substance to be measured in liquid phase by the utilization of optical resonance phenomenon.

The present invention furthermore provides a spectrometric apparatus for the application of the method of the present invention, which comprises:

(a) a pulse laser oscillator for exciting the fluorescent pigment and the substance to be measured, respectively;

(b) an optical delay device for causing delay of any one of pulse laser beams of two kinds of wavelengths generated by the pulse laser oscillator;

(c) a microscope system for condensing laser beams generated by the pulse laser oscillator and irradiating the condensed beams to the sample; and (d) a detector for detecting light emission of the sample.

Figure 1:
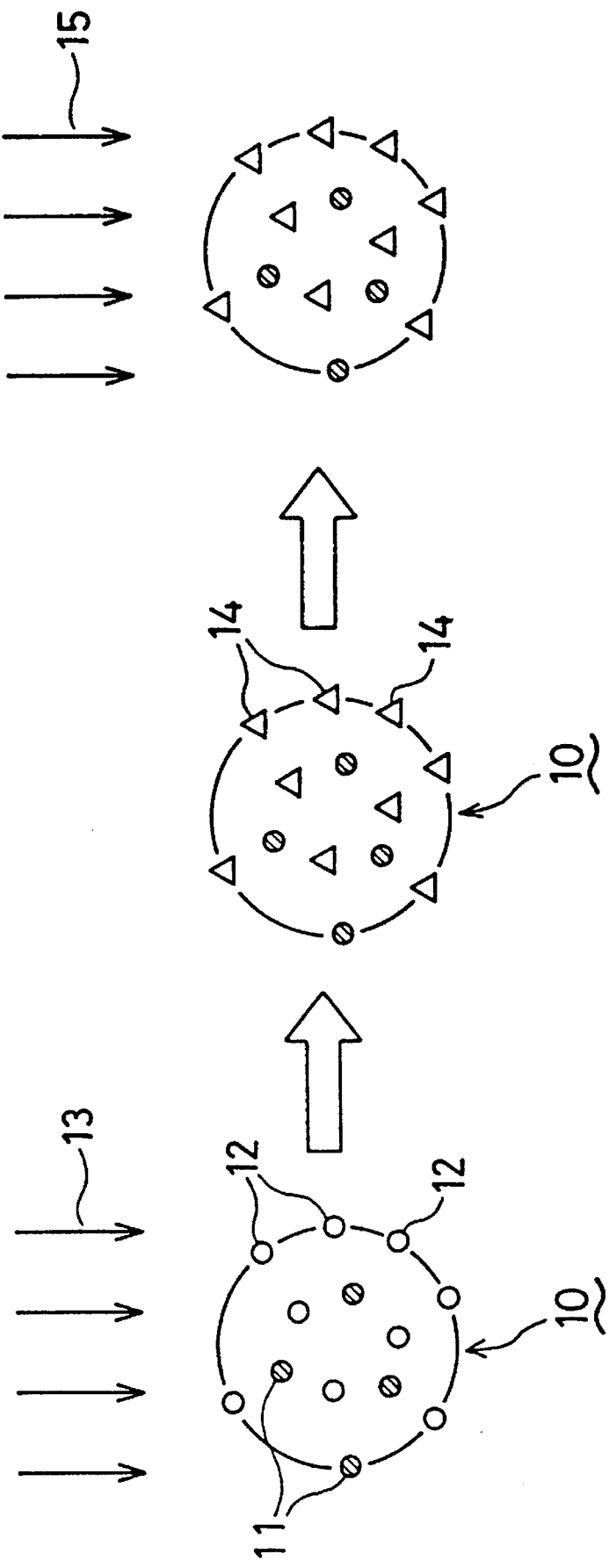
FIG. 1 is a schematic view illustrating the principle of measurement in the method and the apparatus therefor of the present invention.

In the drawings, the reference numerals represent the following components:

1: CW laser oscillator
2: Pulse laser oscillator
3: Optical delay device
4: Microscope system
4a: Objective
4b: Sample holder
5: Detector
6: Lens
7a: Exciting laser beam reflecting mirror
7b: Trapping laser beam reflecting mirror
7c: Exciting laser beam/pumping laser beam/trapping laser beam reflecting mirror
8: Mirror
10: Particulates
11: Fluorescent pigment
12: Substance to be measured
13: Exciting laser beam
14: Intermediate product
15: Pumping laser beam
20: Trapping laser beam
21: Pumping laser beam
22: Exciting laser beam

DETAILED DESCRIPTION OF THE INVENTION

Because the optical resonance of particulates is utilized in the method of the present invention as described above, it is possible to adopt a very long optical path as compared with the particle size, and hence to measure absorbance at a high sensitivity.

More specifically, a spherical-shaped particulate having a higher refractive index than the surrounding medium and comprising a transparent material is known to serve as an optical resonator at the wavelength satisfying condition. With a plurality of resonance wavelengths intrinsic to the shape and size of particulates, the light beam is efficiently captured in the optical resonator, and propagates through the particulates. With these resonance wavelengths, Q-values (indices expressing performance of a resonator) of from $10^3$ to $10^5$ are easily available, and the lengths of optical paths corresponding to these Q-values are of the order of from mm to even cm for a particulate diameter of the order of μm. It is therefore possible to obtain an optical path the from $10^2$ to $10^4$ times as long as diameter.

Optical resonance phenomenon takes place very efficiently in this case by doping a fluorescent substance to the particulates, causing light emission of the fluorescent substance through optical exciting from outside, and using the emitted light beam from the fluorescent substance near interfaces of the particulates where a resonator is formed. Doping of a substance hindering optical resonance (absorbance), i.e., a substance to be measured, simultaneously to the particulates permits high-sensitivity measurement of absorbance. The particulates can now be optically trapped.

More particularly, in an embodiment of the method of spectrometry of the present invention, as shown in FIG. 1, particulates (10) in liquid phase capable of being optically trapped by a CW laser beam or the like previously contain a substance to be measured (12) together with a fluorescent substance (11). The substance to be measured (12) is optically excited with an exciting beam (13) to produce an intermediate product (14) having absorbance at the resonance wavelength of the particulates (10). A pumping beam (15) for causing light emission of the fluorescent substance (11) is irradiated onto the particulates offer a delay of a prescribed period of time from the exciting beam. If the pumping beam (15) is irradiated when the intermediate products (14) exist in the particulates, optical resonance of the particulates taking place along the optical path is impaired by the absorption of the intermediate products (14). The result of impaired optical resonance takes the form of a change in the light emission.

The transient absorbance during the prescribed delay time is thus measured at a high sensitivity from the change in the light emission at the optical resonance wavelength of the particulates based on the presence of the pumping beam (15).

In addition, it is also possible to obtain a plurality of oscillation lines by properly selecting conditions such as the particulate diameter and the concentration of the fluorescent pigment, thus enabling measurement of the transient absorption spectrum at a high sensitivity from the change in the oscillation intensity.

Utilization of optical resonance of particulates permits spectrometric measurement as described above. Particularly, use of laser oscillation from among optical resonance phenomena leads to successful measurement with an excellent S/N.

EXAMPLES

Figure 2:
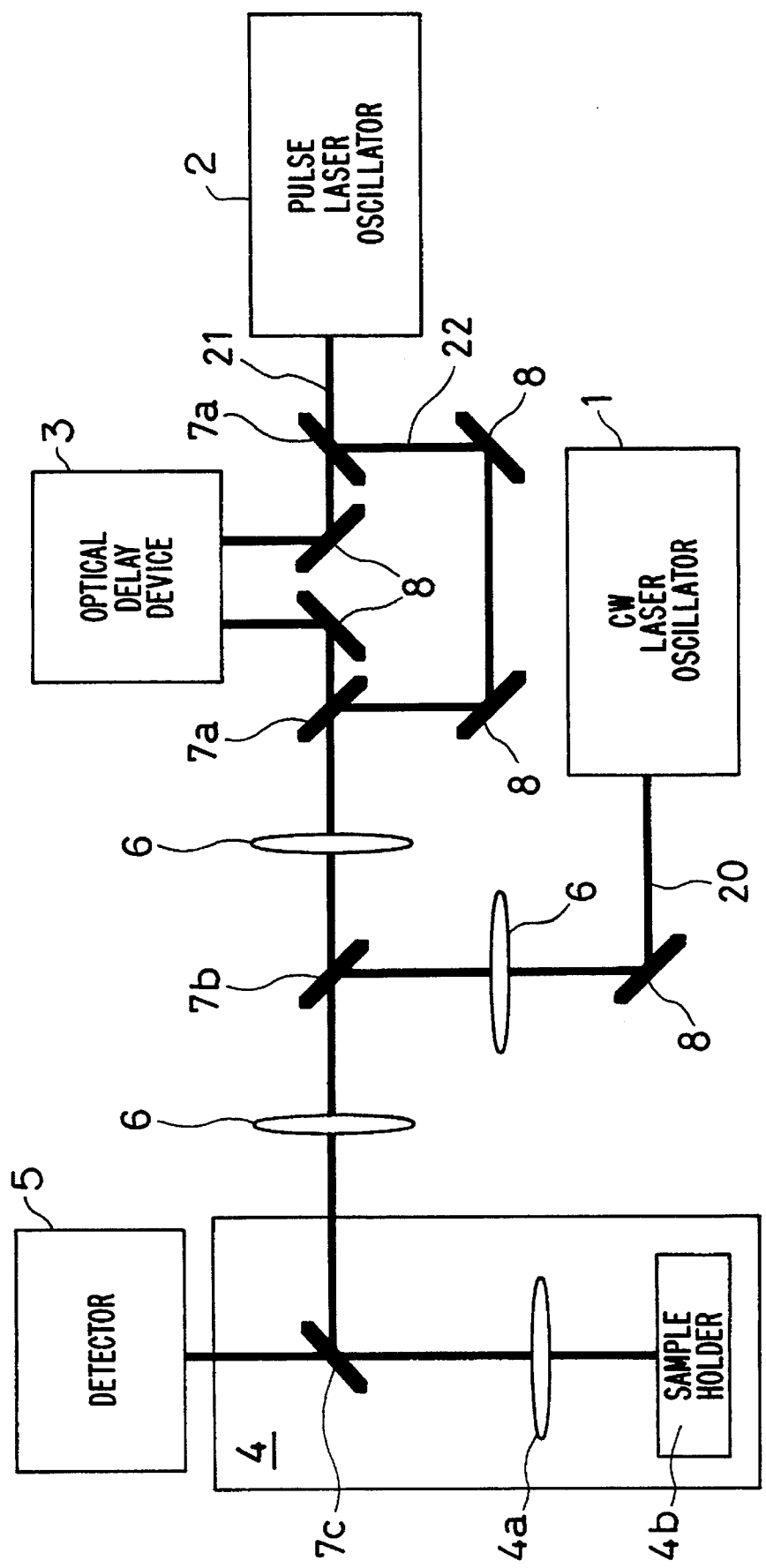
FIG. 2 is a schematic view illustrating embodiments of the method and the apparatus therefor of the present invention.

The construction shown in FIG. 2 may be presented as an embodiment of the spectrometric apparatus of the present invention. More specifically, the spectrometric apparatus comprises a pulse laser oscillator (2) for exciting the fluorescent pigment and the substance to be measured, contained in the particulates in liquid phase, an optical delay device (3) for causing delay of any one of pulse laser beams of two wavelengths generated from this pulse laser oscillator (2), a CW laser oscillator (1) for non-contact trapping and fixing the particulates in liquid phase, a microscope system (4) which collects these laser beams and irradiates them onto the sample, and a detector (5) for detecting light emission from the sample. Provision of the CW laser oscillator (1) is not limitative, but any appropriate means capable of non-contact trapping and fixing the particulates may be adopted.

As shown in FIG. 2, the apparatus of the present invention may be provided, along the optical path for irradiation of laser beams, with a lens (6), an exciting laser reflecting mirror (7a), a trapping laser reflecting mirror (7b) and a mirror (8). The microscope system (4) may be provided with an exciting laser beam/pumping laser beam/trapping laser beam reflecting mirror (7c), an objective (4a) and a sample stand or holder (4b).

When a CW laser oscillator (1) for trapping particulates is used, a CW-YAG laser beam (wavelength: 1,064 nm) may be used as the laser beam (20). As the exciting laser beam (22) of the substance to be measured, the third high-frequency wave of Q-switch YAG laser may be used, and as the pumping laser beam (21), the second high-frequency wave of Q-switch laser may be used. The same laser beam for both the exciting laser beam (22) and the pumping laser beam (21) leads to easier matching of timing. The present invention is not however limited to this.

In the embodiment shown in FIG. 2, an optical delay device (3) is provided along the optical path for the pumping laser beam (21) with a view to achieving a prescribed delay time of the pumping laser beam (21) relative to the exciting laser beam (22). This device may of course be provided along the optical path for the exciting laser beam (22). The sample particulates in liquid phase are placed under the microscope, and the three above-mentioned laser beams uniaxed by the mirrors such as dichroic ones are condensed by the objective (4a) of the microscope system (4) and irradiated onto the sample on the sample stand (4b). The light emitted from the sample is collected by the objective (4a) and detected by the detector (5).

In the apparatus described above, 9,10-diphenyl anthracene in a concentration of $2\times10^{-3}$ mol/l as the substance for producing an intermediate product through excitation and Rhodamine B in a concentration of $9\times10^{-3}$ mol/l as the fluorescent pigment were doped to, for example, spherical particulates, having a diameter of 30 µm, comprising poly (methyl methacrylate) (refractive index: 1.49).

A pumping laser beam (wavelength: 532 nm, pulse width; 40 ps, energy: 51 µJ) condensed to about 60 µm by the objective (100 magnifications) was irradiated onto the particulates dispersed in water.

Figure 3:
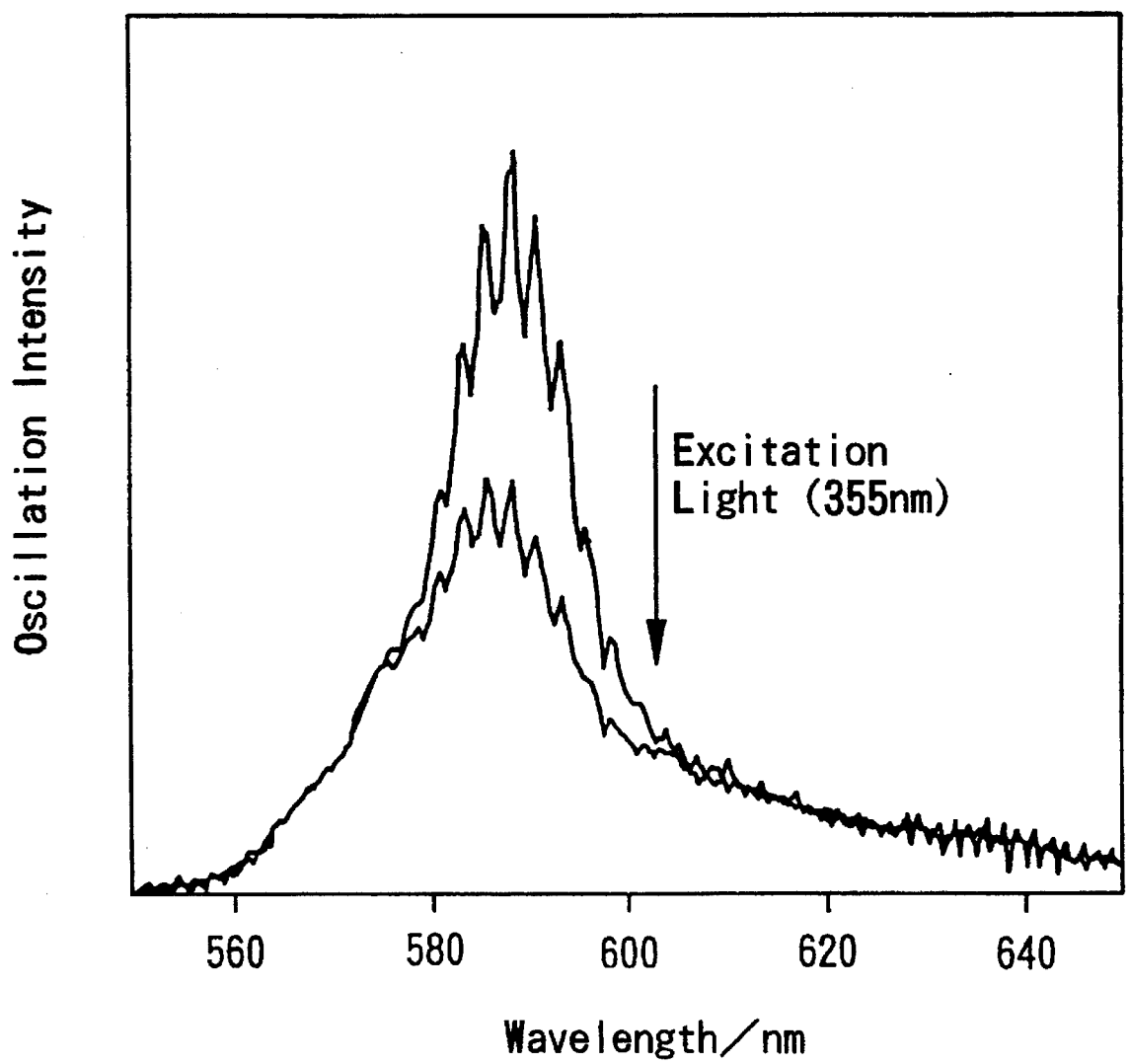
FIG. 3 is a graph illustrating the relationship between the intensity of an excited beam and the oscillation spectrum in an example of the present invention.

The results are shown in FIG. 3. Seven to eight laser oscillation peaks from the particulates were observed around 590 nm. By condensing and irradiating the exciting beam (wavelength: 355 nm, pulse width: 40 ps, energy: 1.3 mJ) by means of the same optical system prior by several hundred ps to the pumping laser beam, the laser oscillation intensity was attenuated, thus permitting measurement of absorbance in excitation of diphenyl anthracene on particulate interfaces, which could not conventionally be measured.

According to the present invention, as described above in detail, it is possible to measure transient absorbance and transient absorption spectrum at a high sensitivity even when particulates containing the substance to be measured in liquid phase are present.

What is claimed is:

1. A method for spectrometric measurement of particulate surfaces of a particulate substance, comprising the steps of:

doping the particulate substance with a fluorescent substance;

irradiating a light beam onto the particulate substance doped with the fluorescent substance; and measuring transient absorbance and transient absorption spectrum of the particulate substance at particulate interfaces in liquid phase by detecting optical resonance phenomena of the irradiated particulate substance and the irradiated fluorescent substance.

2. A method as claimed in claim 1, wherein the optical resonance phenomenon of the irradiated particulate substance is the status of laser oscillation.

3. A method as claimed in claim 2, wherein said step of measuring is conducted by optically trapping the particulate substance.

4. A method as claimed in claim 1, wherein said step of measuring is conducted by optically trapping the particulate substance.

5. A spectrometric apparatus for measuring transient absorbance and transient absorption spectrum of a particulate substance at particulate interfaces in liquid phase, wherein the particulate substance is doped with a fluorescent pigment, by the utilization of optical resonance phenomena, said apparatus comprising:

(a) a pulse laser oscillator for generating laser beams of two wavelengths and exciting the fluorescent pigment and the substance to be measured, respectively;

(b) an optical delay device for causing delay of laser beams of one of the two wavelengths generated by said pulse laser oscillator;

(c) a microscope system for condensing laser beams generated by the pulse laser oscillator and irradiating the condensed beams to the particulate substance and the fluorescent pigment; and (d) a detector for detecting light emission of the particulate substance and the fluorescent pigment.

* * * * *